United States Patent
Lantero et al.

(10) Patent No.: US 6,942,997 B2
(45) Date of Patent: Sep. 13, 2005

(54) PROCESS FOR THE PREPARATION OF GLUCONIC ACID AND GLUCONIC ACID PRODUCED THEREBY

(75) Inventors: Oreste J. Lantero, Goshen, IN (US); Jayarama K. Shetty, Pleasanton, CA (US)

(73) Assignee: Genencor International, Inc., Palo Alto, CA (US)

( * ) Notice: Subject to any disclaimer, the term of this patent is extended or adjusted under 35 U.S.C. 154(b) by 6 days.

(21) Appl. No.: 10/613,221

(22) Filed: Jul. 2, 2003

(65) Prior Publication Data

US 2004/0077062 A1 Apr. 22, 2004

Related U.S. Application Data

(63) Continuation of application No. 09/835,241, filed on Apr. 12, 2001, now abandoned, which is a continuation of application No. 08/950,815, filed on Oct. 15, 1997, now abandoned.

(51) Int. Cl.$^7$ .............................. C12P 7/40; C12P 7/00; C12P 7/58
(52) U.S. Cl. ...................... 435/136; 435/132; 435/137
(58) Field of Search ................................ 435/136, 137; 424/489, 490

(56) References Cited

U.S. PATENT DOCUMENTS

| | | | | |
|---|---|---|---|---|
| 2,767,146 A | * | 10/1956 | Bonewitz et al. | 510/442 |
| 2,804,432 A | * | 8/1957 | Bonewitz et al. | 510/442 |
| 3,935,071 A | * | 1/1976 | Bergmeyer et al. | 435/137 |
| 4,460,686 A | * | 7/1984 | Hartmeier | 435/137 |
| 5,767,057 A | * | 6/1998 | Merz et al. | 510/452 |
| 5,897,995 A | * | 4/1999 | Vroemen et al. | 435/137 |

FOREIGN PATENT DOCUMENTS

WO     WO 95/33631     * 12/1995

* cited by examiner

*Primary Examiner*—Christopher R. Tate
(74) *Attorney, Agent, or Firm*—Jones Day

(57) ABSTRACT

An enzymatic system comprised of glucose oxidase and a catalase of the same or different sources to result in the complete conversion of glucose to gluconic acid at a glucose concentration greater than 25% (w/w) ds. The resultant gluconic acid, which is essentially free from impurities normally associated with the fermentation process, is then spray granulated to produce a low-dust dry product.

19 Claims, No Drawings

PROCESS FOR THE PREPARATION OF GLUCONIC ACID AND GLUCONIC ACID PRODUCED THEREBY

This application is a continuation of application Ser. No. 09/835,241, filed Apr. 12, 2001, now abandoned, which is a continuation of application Ser. No. 08/950,815, filed Oct. 15, 1997, now abandoned.

FIELD OF THE INVENTION

The present invention relates to processes for the enzymatic conversion of glucose to gluconic acid, the gluconic acid produced thereby, the preparation of a granular gluconic acid product and the granular product so produced.

BACKGROUND OF THE INVENTION

Gluconic acid, an oxidation product of glucose, has been extensively used in applications as varied as metal cleaning operations in the dairy industry; alkaline bottle washing operations; alkaline derusting operations in the metallurgic industry; and iron deposition prevention in the textile industry. Furthermore, the sodium salt of gluconic acid is used as an additive in cement mixtures.

The production of gluconic acid from glucose may be achieved by the use of processes which may be broadly classified as being either microbial fermentation, electrochemical, chemical and enzymatic (wherein enzymatic systems are employed separately from their source microorganism(s)). While microbial fermentation has perhaps been the most widely employed of these methods, it nonetheless suffers many drawbacks, including those associated with process conditions required for the fermentation microorganisms used, which has limited its commercial applicability.

The enzymatic conversion of glucose to gluconic acid involves treating a glucose bearing material with an enzyme preparation having glucose oxidase and catalase activity. This reaction is performed in the presence of a free oxygen source, such as hydrogen peroxide. Generally, the glucose-bearing material is in the form of an aqueous solution.

To insure that the glucose oxidase functions at its most effective level, during enzymatic conversion the pH of the reaction media is controlled so as to favor the desired reaction. In the glucose oxidase conversion of glucose, acid (gluconic) is continuously formed. Thus, it is necessary to continuously regulate the pH of the reaction media throughout the enzymatic conversion. Generally, if the pH is maintained between about 4.2 and about 7 (preferably, between about 5 and about 6), the conversion proceeds satisfactorily. A common method of regulating the pH involves the continuous addition of an alkali, such as sodium hydroxide. The alkali neutralizes the gluconic acid to a corresponding gluconate, e.g., sodium gluconate. Examples of enzymatic processes for the production of gluconic acid from glucose using a glucose oxidase/catalase enzyme system can be found in, for example, U.S. Pat. No. 2,651,592 and Romanian Patent No. 92,739.

While being useful for their particular purposes, these enzymatic processes suffer from several drawbacks.

A primary drawback associated with fermentation processes is that the reaction process generally results in the crude reaction broth containing gluconic acid along with other impurities including biomass. This reaction broth must then be purified by multi-step processes including biomass separation (filtration), carbon treatment (decolorization), evaporation (concentration) and crystallization (purification) to provide a final product with high purity.

Another drawback is the presence of residual mother liquid in the reaction broth which must be either recycled, further purified and/or disposed of, thereby adding to the problems and costs of such fermentation conversion processes.

A further drawback associated with enzymatic processes is that they have a low conversion efficiency. This feature results in incomplete conversion of glucose to gluconic acid leaving residual unconverted glucose as a contaminant in the gluconic acid solution produced thereby. In order to reduce or eliminate such unconverted glucose from the final product, costly downstream, separation, recovery and purification steps must be employed.

To alleviate problems associated with incomplete conversion, resort has been had to limiting the glucose concentrations of the starting material to less than 30% weight to weight (w/w) dissolved solids (ds.). Unfortunately, such low glucose concentrations in the starting material are unsatisfactory in that they greatly reduce the efficiency of the process, negatively impacting on its commercial desirability.

Alternatively, resort has been made to interrupting the process prior to the completion thereof. For example, in the processes disclosed in the aforesaid United States patent, the reaction was stopped after converting only 50% of the glucose to gluconic acid. Nonetheless, the reaction mixture still needs to be subjected to electrodialysis to separate and recover the gluconic acid from the residual unconverted glucose and purification of the gluconic acid produced by such processes remains difficult and costly, especially where the glucose is present.

Another drawback associated with enzymatic processes is the use of hydrogen peroxide ($H_2O_2$) as a source of oxygen. As an acid, the presence of $H_2O_2$ necessitates constant monitoring of the pH of the reaction solution, as well as the employment of a buffer (such as calcium carbonate in the form of lime) to maintain the solution in a pH range which is acceptable (about 5–6) for the conversion reaction. Furthermore, the use of hydrogen peroxide as the oxygen source results in the by-product formation of large quantities of yet more hydrogen peroxide and acids, necessitating the use of yet more catalases (to convert the hydrogen proxides formed into water and oxygen) and pH neutralizers.

Accordingly, it can be seen that there remains a need for the provision of enzymatic processes for the production of gluconic acid from glucose wherein dissolved glucose solid concentrations of 30% (w/w) ds. (dissolved solids) and higher may be used while still obtaining high conversion rates, wherein reduced quantities of buffers, such as sodium hydroxide, need to be employed, wherein the use of extensive and/or expensive downstream, separation, recovery and/or purification processes and/or apparatuses need not be employed and which permits the production of spray-dried and essentially pure gluconic acid granules without employing crystallization processes.

SUMMARY OF THE INVENTION

It is a primary object of the present invention to provide an enzymatic process for the production of gluconic acid from glucose wherein dissolved solid concentrations of glucose of 30% (w/w) ds. and higher may be used while still enjoying high conversion rates (such as those approaching 100%), which does not require extensive expensive downstream separation, recovery and/or purification, which permits the production of spray-dried and essentially pure granular gluconic acid without employing crystallization processes.

It is a further object of the present invention to provide such a process wherein the final gluconic acid solution produced thereby, has a low concentrations of impurities, including residual unconverted glucose.

It is a still further object of the present invention to provide such a process wherein low (reduced) quantities of buffers, such as sodium hydroxide, need to be employed.

A yet further object of the present invention is to provide processes for producing a dry, low-dust, granular gluconic acid product without the necessity of employing a crystallization process.

In another aspect of the present invention, it is an object herein to provide a substantially pure gluconic acid solution.

A still yet further object of the present invention is to provide a dry, low-dust, granular gluconic acid product.

In accordance with the teachings of the present invention, disclosed herein is a process for the enzymatic conversion of glucose to gluconic acid. This process includes providing a solution of glucose. The process further includes adding to the solution, in the presence of an oxygen source, from about 25 to about 30 glucose oxidase units (GOU) of glucose oxidase/gram ds. of glucose in the solution and at least 1200 catalase units (CU) of catalase/gram ds. of glucose in the solution. In this fashion, the glucose is enzymatically converted to gluconic acid.

Preferably, the solution of glucose has from about 25% (w/w) ds. of glucose to about 60% (w/w) ds. of glucose and, more preferably, from about 30% (w/w) ds. of glucose to about 50% (w/w) ds. glucose.

In a preferred embodiment, about 27 GOU of glucose oxidase/gram ds. of glucose in the solution is added to the solution.

Preferably, from about 1279 to about 1999 CU of catalase/gram ds. of glucose in the solution is added to the solution.

In one preferred embodiment, at least 1279 CU of catalase/gram ds. of glucose in the solution is added to the solution.

In a second preferred embodiment, at least 1559 CU of catalase/gram ds. of glucose in the solution is added to the solution.

In a third preferred embodiment, at least 1999 CU of catalase/gram ds. of glucose in the solution is added to the solution.

Preferably, the glucose oxidase and the catalase are added to the solution of glucose in two equal doses, the first dose being added at the start of the reaction (log 0 hours) and the second dose being added halfway (50%) through the total time of the intended reaction.

In another preferred embodiment, the glucose oxidase and the catalase are added to the solution of glucose in three equal doses, the first dose being added at the start of the reaction (log 0 hours), the second dose being added one-third through the total time of the reaction and the third dose being added two-thirds through the total time of the reaction.

Preferably, the catalase is naturally produced by a strain of the species *Aspergillus niger*.

Preferably, the solution of glucose is maintained at a pH of from about 5 to about 7 throughout the reaction and, more preferred, the solution of glucose is maintained at a pH of 6 throughout the reaction.

Preferably, the temperature of the solution of glucose is maintained at from about 25° C. to about 40° C. throughout the reaction, and, more preferred, the solution of glucose is maintained at from about 30° C. to about 35° C. throughout the reaction.

Preferably, the pressure of the solution of glucose is maintained at about 1 bar throughout the reaction.

Preferably, the air flow through the solution of glucose is maintained at about 1 vvm throughout the reaction.

In a particularly preferred embodiment disclosed herein, the process for the enzymatic conversion of glucose to gluconic acid includes providing a solution of glucose having from about 25% (w/w) ds. of glucose to about 60% (w/w) ds. of glucose. The process further includes adding to the solution, in the presence of an oxygen source, from about 25 to about 30 GOU of glucose oxidase/gram ds. glucose in the solution and from about 1279 to about 1999 CU of catalase/gram ds. glucose in the solution while, throughout the reaction, maintaining the solution of glucose at a pH of about 5 to about 7, at a temperature of about 25° C. to about 40° C., at a pressure of about 1 bar and at an air flow of about 1 volume gas per volume of reaction medium per minute (vvm).

Finally, and in another aspect of the present invention disclosed herein is a process for the preparation of a dry, spray-granulated gluconic acid product and the product produced thereby.

In this regard, the gluconic acid-containing solution, produced as described above, is concentrated and filtered, whereby gluconic acid crystals (as sodium gluconate) are obtained. The crystals are then sprayed-coated with liquid sodium gluconate in a spray-dryer, whereby a spray-granulated gluconic acid is obtained.

DESCRIPTION OF PREFERRED EMBODIMENTS

The disclosed process for the enzymatic conversion of glucose to gluconic acid permits the enzymatic conversion of glucose solutions having a dissolved (glucose) solids content of greater than 25% (w/w) ds. of glucose without the resulting build-up of residual unconverted glucose in the gluconic acid solution produced thereby and with the use of reduced quantities of buffers, such as sodium hydroxide, which must be employed.

Furthermore, use of the principles disclosed herein permits the fashioning of such processes which do not require the use of extensive and/or expensive downstream, separation, recovery and/or purification processes and/or apparatuses and which permit the production of spray-dried and essentially pure gluconic acid without employing crystallization processes and which permits the formation of spray-dried granulation of the gluconic acid obtained thereby.

The processes of the present invention produce spray-granulated gluconic acid and pure gluconic acid without the need to employ crystallization or purification processes.

The process of the present invention permits the efficient enzymatic conversion of glucose to gluconic acid. This process includes providing a solution of glucose. As taught herein, this process is useful with solutions having glucose concentrations greater than 25% (w/w) ds. of glucose. Preferably, the solution of glucose has from about 25% (w/w) ds. of glucose to about 60% (w/w) ds. of glucose. Particularly good results are obtained by use of glucose solutions having from about 30% (w/w) ds. of glucose to about 50% (w/w) ds. of glucose.

The process further includes adding to the solution, in the presence of an oxygen source, from about 25 to about 30 GOU of glucose oxidase/gram ds. glucose in the solution. Preferably, about 27 GOU to about 29 GOU of glucose oxidase/gram ds. of glucose in the solution is employed. In one embodiment about 28.6 GOU of glucose oxidase/gram ds. of glucose in the solution is employed.

As used herein, one glucose oxidase unit is defined as being the amount of enzyme required to oxidase one micromole of D-glucose per minute under the assay conditions 25° C. and pH 7.0.

The process further includes adding to the solution, in the presence of an oxygen source, and at least 1200 CU of catalase/gram ds. of glucose in the solution. Preferably, from about 1279 to about 1999 CU of catalase/gram ds. of glucose in the solution is added to the solution. In particular preferred embodiments, at least 1279, 1559 and 1999 CU of catalase/gram ds. of glucose in the solution is added to the solution.

As used herein, one catalase unit is defined as being the amount of enzyme required to decompose $1\mu$ mole of hydrogen peroxide per minute under the assay conditions 25° C. and pH 7.0.

Any suitable catalase may be employed in the process of the present invention. Catalases which are naturally produced by (or derived from) strains of *Aspergillus niger* and *Micrococcus lysodeikticus*, as well as catalases produced by mamilian sources, such as bovine sources, may be employed. In this context, we have found herein that the catalase which is naturally produced by stains of the species *Aspergillus niger* is particularly efficacious.

Preferably, the glucose oxidase and the catalase are added to the solution of glucose in equal doses. In this regard, in one embodiment herein, the glucose oxidase and the catalase are added to the solution of glucose in two equal doses, the first dose being added at the start of the reaction (log 0 hours) and the second dose being added halfway (50%) through the total time of the intended reaction To illustrate this point, if the reaction is to proceed for 24 hours then, in that event, the first dose would be added at the start of the reaction and the second dose would be added at the start of the 13th hour.

Further in this regard, in a second embodiment, the glucose oxidase and the catalase are added to the solution of glucose in three equal doses, the first dose being added at the start of the reaction (log 0 hours), the second dose being added one-third (33.3%) through the total time of the intended reaction and the third dose being added two-thirds (66.6%) through the total time of the intended reaction. To illustrate this point, if the reaction is to proceed for 24 hours then, in that event, the first dose would be added at the start of the reaction and the second dose would be added at the start of the nineth hour and the third dose would be added at the start of the 17th hour.

The solution of glucose may be maintained at any pH which permits the reaction to occur. However, it is preferred herein that the solution of glucose be maintained at a pH of from about 5 to about 7 throughout the reaction. Most preferred is maintaining the solution of glucose at a pH of 6 throughout the reaction.

The solution of glucose may be maintained at any temperature which permits the reaction to occur. However, in this regard, it is preferred that the temperature of the solution of glucose is maintained at from about 25° C. to about 40° C. throughout the reaction. Most preferred is maintaining the solution of glucose at from about 30° C. to about 35° C. throughout the reaction.

While the solution of glucose may be maintained at any pressure which permits the reaction to occur, it is preferred that the presssure of the solution of glucose is maintained at about 1 bar throughout the reaction.

While the solution of glucose may be maintained by passing air through the glucose solution at any flow rate which permits the reaction to occur, it is preferred herein that the rate of air flow through the solution of glucose be maintained at about 1 vvm throughout the reaction.

Having thus described the processes of the present invention for the enzymatic conversion of glucose to gluconic acid, the gluconic acid produced thereby and processes for producing a spray-granulated gluconic acid product, reference is now made to the following examples which are presented herein for the purposes of illustration only and are neither meant to be, nor should they be read as being, restrictive.

Unless otherwise specified herein, the Examples of the present invention were performed with the use of glucose oxidase from *Aspergillus niger* (sold by SOLVAY ENZYMES, GmbH, Germany), catalase from *Micrococcus lysodeikticus* sold under the trademark MicroCatalase L-1000 (SOLVAY ENZYMES, Inc., Elkhart, Ind.) and crystalline glucose marketed under the name StaleyDex 333 R (Staley, USA).

EXAMPLE 1

Effect of pH

The effect of pH on the conversion of glucose to gluconic acid by glucose oxidase-catalase enzyme system according to the method of the present invention, was studied at a glucose concentration of 40% (w/w) ds.

8 liters of 40% (w/w) ds. glucose solution was prepared and introduced into a 10 liter fermentor (Chempec, Inc., New Jersey, USA). The pH was adjusted to pH 4.0 with dilute acid (i.e., 5N sulfuric acid) or alkali (i.e., 4N sodium hydroxide), as necessary.

The reaction was carried out at 35° C. with a pressure at 1 bar and air was bubbled at a rate of 1 VVM. The pH was maintained at the specified pH during the reaction by the addition of 50% (w/w) sodium hydroxide. Foam was controlled by the addition of antifoam MAZU DF6000 (PPG/MAZER CHEMICALS) (80–120 ppm).

Doses of 12.25 glucose oxidase units (GOU) per gram of dissolved solids of glucose of the solution and 726.8 catalase units (CU) per gram of dissolved solids of glucose of the solution were added to the fermentor at log 0 and at log 12 hours.

The conversion of glucose to gluconic acid was measured by determining the milliequivalent of sodium hydroxide consumed and/or by analyzing the samples using high pressure liquid chromatographic (HPLC) method.

HPLC analysis was carried out using an HPLC system consisting of Beckman 112 Solvent Delivery Module (BECKMAN, USA) fitted to a RI detector Model ERC-7515A, (The ANSPEC Co., Inc., USA) Glucose and gluconic acid were separated using an HPX 87-C column (Bio-Rad, USA) at 80° C. and 0.01M calcium acetate (pH 5.5) was used as the mobile phase at a flow rate of 1 ml/min.

The color impurities were determined by measuring the absorbance (optical density) of 37.5% (w/w) solution gluconic acid in 5% (w/w) NaOH solution at 470 nm.

Four additional experiments were then conducted using the same protocol, and under the same process conditions, as described above with the exception that the pH of the reaction mixture was for each experiment to, respectively, pH 5.0, pH 6.0, pH 7.0 and pH 8.0.

The effects of different pHs on the efficiency of the conversion of glucose to gluconic acid are summarized below in Table 1.

TABLE 1

Effect of pH on the Conversion of Glucose to Gluconic Acid using Glucose Oxidase-Catalase Enzyme System

| Reaction Time | Per Cent Conversion | | | | |
|---|---|---|---|---|---|
| (Hours) | pH 4.0 | pH 5.0 | pH 6.0 | pH 7.0 | pH 8.0 |
| 1 | 2.6 | 6.8 | 5.1 | 5.0 | 3.3 |
| 2 | 3.7 | 14.2 | 14.9 | 13.1 | 5.6 |
| 3 | 5.2 | 22.4 | 32.1 | 20.2 | 8.0 |
| 4 | 4.6 | 29.0 | 30.3 | 26.7 | 10.0 |
| 5 | 4.8 | 35.1 | 36.7 | 32.5 | 11.8 |
| 6 | 4.8 | 40.6 | 42.5 | 34.1 | 13.4 |
| 7 | 4.8 | 45.3 | 47.2 | 40.5 | 15.0 |
| 8 | 4.8 | 49.1 | 51.3 | 45.5 | 16.5 |
| 9 | 4.8 | 52.5 | 54.8 | 48.9 | 17.9 |
| 10 | 4.8 | 55.9 | 57.9 | 55.3 | 19.5 |
| 11 | 4.8 | 61.8 | 60.8 | 61.2 | 22.0 |
| 12 | 4.8 | 67.6 | 64.8 | 66.6 | 24.4 |
| 13 | 4.8 | 73.2 | 71.7 | 71.7 | 26.7 |
| 14 | 4.8 | 78.5 | 78.1 | 77.1 | 29.0 |
| 15 | 4.8 | 84.0 | 83.8 | 81.1 | 31.2 |
| 16 | 4.8 | 88.8 | 89.0 | 84.8 | 33.4 |
| 17 | 4.8 | 93.4 | 94.3 | 87.9 | 35.5 |
| 18 | 4.8 | 97.4 | 99.2 | 91.5 | 39.3 |
| 19 | 4.8 | 99.3 | 100.0 | 94.9 | 41.2 |
| 20 | 4.8 | 99.6 | 100.0 | 98.2 | 45.2 |
| 21 | 4.8 | 99.9 | 100.0 | 99.9 | 46.9 |
| 22 | 4.8 | 99.9 | 100.0 | 100.0 | 48.5 |
| 23 | 4.8 | 100.0 | 100.0 | 100.0 | 50.2 |
| 24 | 4.8 | 100.0 | 100.0 | 100.0 | 51.9 |

Table 1 shows that, at pHs of between 5 and 7, using the method of the present invention achieves a 100% conversion of glucose to gluconic acid in less than 24 hours.

EXAMPLE 2

Enzyme Dosage—Single Addition and Multiple Addition

The effect of adding the glucose oxidase and catalase in either one or several doses throughout the reaction on the conversion of glucose to gluconic acid according to the method of the present invention was determined by performing three experiments wherein the protocols and process conditions were maintained the same, with the exceptions of timing and manner of the dosing of the enzymes.

The conversion of glucose to gluconic acid was carried out in three separate experiments using the same protocol and under the same process conditions as described above in Example 1, but with the following exceptions: the reaction mixtures of all experiments were maintained at pH 6.0; and the quantities and timing of the enzyme additions were varied. In that regard, the total concentration of glucose oxidase and catalase added was maintained constant (at 27 glucose oxidase units per gram of dissolved glucose solids and 1599 catalase units per gram of dissolved glucose solids) but were added in either one, two or three doses.

As regards the quantity and time of the enzyme addition in the first experiment 27 GOU/gram ds. and 1599 CU/gram ds. were added at log 0 hours; in the second experiment, 13.5 GOU/grams ds. and 799.5 CU/gram ds. were added at log 0 and at log 12 hours; and in the third experiment, 9 GOU/gram ds. and 533 CU/gram ds. were added at log 0, log 6 and log 12 hours.

The effect of adding the glucose oxidase and catalase in either one or several doses throughout the reaction on the conversion of glucose to gluconic acid are summarized below in Table 2:

TABLE 2

| | Per Cent Conversion | | |
|---|---|---|---|
| Time (Hours) | Experiment #1 | Experiment #2 | Experiment #3 |
| 0 | 0 | 0 | 0 |
| 1 | 3.4 | 5.1 | 4.5 |
| 2 | 13.6 | 14.9 | 11.5 |
| 3 | 22.3 | 23.1 | 17.6 |
| 4 | 30.9 | 30.3 | 23.1 |
| 5 | 38.6 | 36.7 | 27.7 |
| 6 | 45.6 | 42.5 | 31.8 |
| 7 | 51.9 | 47.2 | 37.3 |
| 8 | 59.1 | 51.3 | 43.8 |
| 9 | 64.7 | 54.8 | 49.6 |
| 10 | 69.5 | 57.9 | 54.9 |
| 11 | 72.3 | 60.8 | 60.5 |
| 12 | 73.3 | 64.8 | 65.4 |
| 13 | 74.1 | 71.7 | 71.6 |
| 14 | 74.5 | 78.1 | 77.1 |
| 15 | 74.5 | 83.3 | 82.7 |
| 16 | 74.9 | 89.0 | 88.0 |
| 17 | 74.9 | 94.3 | 93.2 |
| 18 | 75.9 | 99.2 | 97.9 |
| 19 | 75.9 | 100.0 | 99.7 |
| 20 | 75.9 | 100.0 | 100.0 |
| 21 | 75.9 | 100.0 | 100.0 |
| 22 | 75.9 | 100.0 | 100.0 |
| 23 | 75.9 | 100.0 | 100.0 |

EXAMPLE 3

Role of Catalase on the Oxidation of Glucose to Gluconic Acid by Glucose Oxidase The effect of various concentrations of catalase on the conversion of glucose to gluconic acid according to the method of the present invention was determined by performing five experiments wherein the protocols and process conditions were maintained the same with the exception of the catalase concentrations added.

The conversion of glucose to gluconic acid was carried out in five separate experiments using the same protocol and under the same process conditions as described above in Example 2, but with the following exceptions the temperatures of the reaction mixtures were maintained at 40° C.; the concentration of glucose oxidase added was 28.6 GOU/gram ds.; the concentration of the catalase added was varied as will be described below, and all of the catalase and glucose oxidase was added at log 0 time.

As regards to the concentration of the catalase added, the concentration of catalase added was varied, as follows: in the first experiment, 0 catalase units/gram ds. were added; in the second experiment, 959 catalase units/gram ds. were added; in the third experiment, 1279 Catalase units/grams ds. were added; in the fourth experiment, 1559 catalase units/gram ds. were added; and in the fifth experiment, 1999 catalase units/grams ds. were added.

The effect of varying catalase concentrations on the conversion of glucose to gluconic acid under identical conditions are summarized below in Table 3:

TABLE 3

Per Cent Conversion

| Reaction Time (Hours) | 0 CU per g. ds. | 959 CU per g. ds. | 1279 CU per g. ds. | 1559 CU per g. ds. | 1999 CU per g. ds. |
|---|---|---|---|---|---|
| 1 | 1.6 | 3.4 | 4.5 | 3.4 | 4.6 |
| 2 | 5.1 | 13.4 | 13.2 | 13.6 | 14.0 |
| 3 | 6.3 | 22.6 | 22.3 | 22.3 | 22.8 |
| 4 | 6.9 | 30.7 | 31.5 | 30.9 | 31.3 |
| 5 | 7.0 | 38.5 | 39.7 | 38.6 | 39.1 |
| 6 | 7.0 | 45.7 | 47.2 | 45.6 | 46.7 |
| 7 | 7.0 | 51.7 | 53.6 | 51.9 | 53.7 |
| 8 | 7.0 | 56.1 | 59.3 | 59.1 | 59.6 |
| 9 | 7.0 | 57.8 | 64.0 | 64.7 | 65.5 |
| 10 | 7.1 | 58.6 | 66.1 | 69.5 | 71.0 |
| 11 | 7.1 | 59.1 | 67.4 | 72.3 | 75.5 |
| 12 | 7.1 | 59.4 | 68.1 | 73.3 | 79.1 |
| 13 | 7.1 | 59.9 | 68.4 | 74.1 | 80.3 |
| 14 | 7.1 | 59.9 | 68.4 | 74.5 | 81.4 |
| 15 | 7.1 | 59.9 | 68.7 | 74.5 | 81.8 |
| 16 | 7.1 | 59.9 | 68.7 | 74.9 | 81.8 |
| 17 | 7.1 | 59.9 | 68.7 | 74.9 | 82.4 |
| 18 | 7.1 | 59.9 | 68.7 | 75.9 | 82.4 |
| 19 | 7.1 | 59.9 | 68.7 | 75.9 | 82.4 |
| 20 | 7.1 | 59.9 | 68.7 | 75.9 | 82.9 |
| 21 | 7.1 | 59.9 | 68.7 | 75.9 | 82.9 |

The results of Table 3 show that, in the method of the present invention, the inactivation of glucose oxidase by hydrogen peroxide is significantly reduced by the addition of catalase. In the absence of catalase, the oxidation of glucose to gluconic acid by glucose oxidase proceeded for 5 hours with only 7% conversion. The percent conversion of glucose to gluconic acid was increased with increasing concentration of catalase and a maximum conversion of 80% was reached even at high concentration of catalase. The residual unconverted glucose could be due to the stability (half-life) associated with glucose oxidase under the experimental conditions.

EXAMPLE 4

Effect of Temperature on Oxidation of Glucose to Gluconic Acid Using Glucose Oxidase-Catalase Enzyme System The effect of various temperatures on the conversion of glucose to gluconic acid according to the method of the present invention was determined by performing four experiments wherein the protocols and process conditions were maintained the same with the exception of the temperature of the reaction The conversion of glucose to gluconic acid was carried out in four separate experiments using the same protocol and under the same process conditions as described above in Example 2, but with the following exceptions the temperatures of the reaction mixtures were varied, as will be described below, 50% of the glucose oxidase units (13.5 glucose oxidase units) and 50% of the catalase units (799.5 catalase units) were added at log 0 hours and 50% of the glucose oxidase units (13.5 glucose oxidase units) and 50% of the catalase units (799.5 catalase units) were added at log 9 hours.

As regards to the temperatures employed, the temperatures employed were varied, as follows: in the first experiment, the temperature was 25° C.; in the second experiment, the temperature was 30° C.; in the third experiment, the temperature was 35° C.; and in the fourth experiment, the temperature was 40° C.

The effect of the different temperatures on the conversion of glucose to gluconic acid under identical conditions are summarized below in Table 4

TABLE 4

Per Cent Conversion

| Reaction Time (Hours) | 25° C. | 30° C. | 35° C. | 40° C. |
|---|---|---|---|---|
| 0 | 0.0 | 0.0 | 0.0 | 0.0 |
| 1 | 2.6 | 0.0 | 6.5 | 6.1 |
| 2 | 5.3 | 12.0 | 14.4 | 13.8 |
| 3 | 7.9 | 16.7 | 21.5 | 21.5 |
| 4 | 14.0 | 22.1 | 28.2 | 28.3 |
| 5 | 18.0 | 28.2 | 34.4 | 34.6 |
| 6 | 22.0 | 33.4 | 39.7 | 40.0 |
| 7 | 25.2 | 37.3 | 44.2 | 44.4 |
| 8 | 27.5 | 42.1 | 48.2 | 47.6 |
| 9 | 32.8 | 45.4 | 54.4 | 52.5 |
| 10 | 38.6 | 51.3 | 61.1 | 59.9 |
| 11 | 42.4 | 56.5 | 67.4 | 67.1 |
| 12 | 47.9 | 61.8 | 73.6 | 73.9 |
| 13 | 54.0 | 66.8 | 79.5 | 80.4 |
| 14 | 59.6 | 71.7 | 84.7 | 85.1 |
| 15 | 64.8 | 77.0 | 89.5 | 87.2 |
| 16 | 69.5 | 81.2 | 93.1 | 88.0 |
| 17 | 74.2 | 85.3 | 95.7 | 88.5 |
| 18 | 78.1 | 89.6 | 96.7 | 88.7 |
| 19 | 82.9 | 93.3 | 97.0 | 88.8 |
| 20 | 87.0 | 96.8 | 97.6 | 89.0 |
| 21 | 90.9 | 99.2 | 97.7 | 89.0 |
| 22 | 93.7 | 99.7 | 98.0 | 89.0 |
| 23 | 97.2 | 99.9 | 98.0 | 89.0 |
| 24 | 99.1 | 99.9 | 98.0 | 89.0 |
| 25 | 99.1 | 100.0 | 98.0 | 89.0 |

EXAMPLE 5

Effect of Glucose Concentration on the Conversion of Glucose to Gluconic Acid Using Glucose Oxidase-Catalase Enzyme System The effect of various concentrations of glucose on the conversion of glucose to gluconic acid according to the method of the present invention was determined by performing six experiments wherein the protocols and process conditions were maintained the same with the exception of the glucose concentrations added.

The conversion of glucose to gluconic acid was carried out in six separate experiments using the same protocol and under the same process conditions as described above in Example 2, but with the following exceptions the temperatures of the reaction mixtures were maintained at 30° C.; the concentration of the glucose added was varied as will be described below, and all of the catalase and glucose oxidase was added at log 0 time.

The effect of glucose concentration (dissolved solids) on the conversion rate of glucose to gluconic acid by the Glucose oxidase-catalase enzyme was studied as described above in Example 2, but with the glucose concentration being varied, as follows: in the first experiment, the glucose concentration was 30% ds.; in the second experiment, the glucose concentration was 35% ds.; in the third experiment, the glucose concentration was 40% ds.; in the fourth experiment, the glucose concentration was 45% ds.; in the fifth experiment, the glucose concentration was 50% ds.; and in the sixth experiment, the glucose concentration was 55% ds.

The effect of varying glucose concentrations on the conversion of glucose to gluconic acid under identical conditions are summarized below in Table 5:

TABLE 5

Per Cent Conversion

| Reaction Time (Hours) | Glucose Concentration [in % (w/w)] | | | | | |
|---|---|---|---|---|---|---|
| | 30% | 35% | 40% | 45% | 50% | 55% |
| 0 | 0.0 | 0.0 | 0.0 | 0.0 | 0.0 | 0.0 |
| 1 | 7.7 | 4.0 | 0.0 | 3.6 | 2.0 | 0.0 |
| 2 | 17.2 | 12.5 | 12.0 | 8.2 | 6.0 | 4.4 |
| 3 | 26.6 | 22.5 | 16.7 | 13.7 | 9.7 | 6.5 |
| 4 | 34.7 | 31.6 | 22.1 | 18.4 | 13.3 | 8.4 |
| 5 | 41.9 | 39.7 | 28.2 | 22.5 | 16.7 | 10.4 |
| 6 | 47.8 | 47.1 | 33.4 | 25.8 | 20.1 | 12.4 |
| 7 | 53.2 | 53.6 | 37.3 | 30.4 | 23.2 | 14.5 |
| 8 | 57.8 | 59.4 | 42.1 | 34.4 | 26.1 | 16.5 |
| 9 | 61.3 | 64.4 | 45.4 | 37.1 | 29.0 | 18.6 |
| 10 | 68.2 | 71.2 | 51.3 | 39.6 | 31.7 | 20.5 |
| 11 | 78.5 | 79.0 | 56.5 | 42.6 | — | 22.4 |
| 12 | 88.4 | 86.6 | 61.8 | 46.4 | 36.9 | 24.1 |
| 13 | 97.1 | 94.5 | 66.8 | 51.0 | 40.0 | 25.7 |
| 14 | 99.5 | 99.3 | 71.2 | 55.2 | 42.7 | 27.2 |
| 15 | 99.9 | 99.7 | 77.0 | 59.4 | 45.4 | 28.5 |
| 16 | 100.0 | 99.9 | 81.2 | 63.1 | 48.1 | 30.5 |
| 17 | 100.0 | 100.0 | 85.3 | 67.0 | 50.5 | 32.0 |
| 18 | 100.0 | 100.0 | 89.6 | 70.5 | 52.9 | 33.6 |
| 19 | 100.0 | 100.0 | 93.3 | 74.2 | 55.6 | 35.1 |
| 20 | 100.0 | 100.0 | 96.8 | 77.2 | 58.0 | 36.6 |
| 21 | 100.0 | 100.0 | 99.2 | 80.9 | 60.1 | 38.3 |
| 22 | 100.0 | 100.0 | 99.7 | 84.3 | 62.4 | 39.9 |
| 23 | 100.0 | 100.0 | 99.9 | 87.7 | 64.7 | 41.7 |
| 24 | 100.0 | 100.0 | 99.9 | 90.7 | 66.8 | 43.2 |
| 25 | 100.0 | 100.0 | 100.0 | 93.4 | 68.8 | 44.7 |
| 26 | 100.0 | 100.0 | 100.0 | 96.1 | 70.9 | 46.0 |
| 27 | 100.0 | 100.0 | 100.0 | 98.9 | 72.9 | 47.4 |
| 28 | 100.0 | 100.0 | 100.0 | 99.7 | 75.0 | 48.8 |
| 29 | 100.0 | 100.0 | 100.0 | 99.8 | 76.8 | 50.2 |
| 30 | 100.0 | 100.0 | 100.0 | 100.0 | 78.6 | 51.8 |
| 31 | 100.0 | 100.0 | 100.0 | 100.0 | 80.4 | 53.3 |
| 32 | 100.0 | 100.0 | 100.0 | 100.0 | 82.1 | 54.7 |
| 33 | 100.0 | 100.0 | 100.0 | 100.0 | 83.6 | 56.1 |
| 34 | 100.0 | 100.0 | 100.0 | 100.0 | 85.0 | 57.5 |
| 35 | 100.0 | 100.0 | 100.0 | 100.0 | 86.5 | 58.9 |
| 36 | 100.0 | 100.0 | 100.0 | 100.0 | 87.7 | 60.1 |
| 37 | 100.0 | 100.0 | 100.0 | 100.0 | 88.9 | 61.5 |
| 38 | 100.0 | 100.0 | 100.0 | 100.0 | 89.8 | 62.7 |
| 39 | 100.0 | 100.0 | 100.0 | 100.0 | 90.6 | 64.0 |
| 40 | 100.0 | 100.0 | 100.0 | 100.0 | 91.4 | 65.3 |
| 41 | 100.0 | 100.0 | 100.0 | 100.0 | 92.0 | 66.5 |
| 42 | 100.0 | 100.0 | 100.0 | 100.0 | 92.5 | 67.7 |
| 43 | 100.0 | 100.0 | 100.0 | 100.0 | 92.9 | 69.0 |
| 44 | 100.0 | 100.0 | 100.0 | 100.0 | 93.4 | 70.1 |
| 45 | 100.0 | 100.0 | 100.0 | 100.0 | 93.7 | 71.3 |
| 46 | 100.0 | 100.0 | 100.0 | 100.0 | 94.0 | 72.6 |
| 47 | 100.0 | 100.0 | 100.0 | 100.0 | 94.2 | 73.7 |
| 48 | 100.0 | 100.0 | 100.0 | 100.0 | 94.5 | 73.7 |
| 49 | 100.0 | 100.0 | 100.0 | 100.0 | 94.6 | 73.7 |
| 50 | 100.0 | 100.0 | 100.0 | 100.0 | 94.8 | 73.7 |
| 51 | 100.0 | 100.0 | 100.0 | 100.0 | 94.9 | 73.7 |
| 21 | 100.0 | 100.0 | 100.0 | 100.0 | 95.1 | 73.7 |
| 53 | 100.0 | 100.0 | 100.0 | 100.0 | 95.2 | 73.7 |
| 54 | 100.0 | 100.0 | 100.0 | 100.0 | 95.3 | 73.7 |

The results of Table 5 showed a remarkable beneficial effect of dissolved solids on the reaction rate using the method of the present invention. The decrease in the solubility of oxygen with increasing dissolved solids presumably responsible for lower rate. However, by adjusting the enzyme dosage, it is possible to complete the conversion within the specified time. The data in the Table 5 clearly showed that the concentration of oxygen/available oxygen and length of the reaction time (enzyme dosage) greatly influences the overall economics of the process.

EXAMPLE 6

Evaluation of Catalases from Different Sources

Effect of catalases from different sources on the conversion of glucose to gluconic acid by the use of glucose oxidase was studied under identical reaction conditions. The following catalases were used: commercial product of bovine catalase (CATALASE L) sold by SOLVAY ENZYMES, Inc., USA, *Aspergillus niger* catalase from SOLVAY ENZYMES, GmbH (Germany) and *Micrococcus* catalase.

The catalase activity of all samples was measured by spectrophotometrically as described by H. Luck in Methods of Enzymatic Analysis (H. U. Bergmeyer, ed.), 1965, pp. 885–894, Verlag Chemie & Academic Press, New York, London).

The time taken for the absorbance of 10 mM hydrogen peroxide solution (in 0.05M phosphate buffer, pH 7) from 0.45 to 0.40 was measured and used to calculate activity.

The experiments were carried out using the protocol, and under the conditions decribed in Example 2, but with the exception that all of the glucose oxidase and the catalase were added to the glucose solution at log 0 hour.

The results are summarized below in Table 6:

TABLE 6

Per Cent Conversion

| Reaction Time (Hours) | *A. niger* 1137 CU/g · ds. | Bovine 1600 CU/g · ds. | Micrococcus 1600 CU/g · ds. |
|---|---|---|---|
| 0 | 0.0 | 0.0 | 0.0 |
| 1 | 8.6 | 4.3 | 0.0 |
| 2 | 16.9 | 10.6 | 12.0 |
| 3 | 25.1 | 17.6 | 16.7 |
| 4 | 32.8 | 23.6 | 22.1 |
| 5 | 40.1 | 28.9 | 28.2 |
| 6 | 47.1 | 34.0 | 33.6 |
| 7 | 53.7 | 36.7 | 37.3 |
| 8 | 59.9 | 37.9 | 42.1 |
| 9 | 66.1 | 38.6 | 45.4 |
| 10 | 72.6 | 39.1 | 51.3 |
| 11 | 78.2 | 39.3 | 56.5 |
| 12 | 82.9 | 41.1 | 61.8 |
| 13 | 88.7 | 46.7 | 66.8 |
| 14 | 94.3 | 52.2 | 71.2 |
| 15 | 99.7 | 56.8 | 77.0 |
| 16 | 99.9 | 59.4 | 81.2 |
| 17 | 100.0 | 60.7 | 85.3 |
| 18 | 100.0 | 61.6 | 89.6 |
| 19 | 100.0 | 62.0 | 93.3 |
| 20 | 100.0 | 62.3 | 96.8 |
| 21 | 100.0 | 62.5 | 99.2 |
| 22 | 100.0 | 62.5 | 99.7 |
| 23 | 100.0 | 62.5 | 99.9 |
| 24 | 100.0 | 62.5 | 99.9 |
| 25 | 100.0 | 62.5 | 100.0 |
| 26 | 100.0 | 62.5 | 100.0 |

As can be seen from Table 6, both *A. niger* and *Micrococcus* catalases showed a 100% conversion of glucose to gluconic acid but at varying rates. However, bovine catalase reached only 60% conversion. Even though all three enzymes were added at the same dosage, but still observed differences in the rate. This could be due to the differences in the stability of catalases against hydrogen peroxide.

EXAMPLE 7

Evaluation of Different Commercial Glucose Syrups

The effect of different sources of glucose syrups with varying degrees of purity on the conversion of glucose to gluconic acid according to the method of the present invention was determined.

The conversion of different glucose syrups was carried out in three separate experiments using the same protocol and process conditions as those described above in Example 2.

The different glucose syrups used were commercially available glucose syrup with varying degree of purity, as follows: Commercia+1 products of Clintose "L"™ (ADM Corn Processing, USA); Clearsweet™ 99 Refined Liquid Dextrose (Cargill, USA); and Royal R Glucose Liquid, 2637 (Corn Products, USA).

The effects of different glucose syrups on the efficiency of the conversion of glucose to gluconic acid according to the method of the present invention are summarized below in Table 7:

TABLE 7

| Reaction Time (Hours) | Per Cent Conversion | | |
|---|---|---|---|
| | Clintose | Clearsweet | Royal Glucose |
| 0 | 0.0 | 0.0 | 0.0 |
| 1 | 4.5 | 3.7 | 4.5 |
| 2 | 12.5 | 9.8 | 10.8 |
| 3 | 20.2 | 17.1 | 17.3 |
| 4 | 27.2 | 23.1 | 23.2 |
| 5 | 32.8 | 28.6 | 28.7 |
| 6 | 38.0 | 33.3 | 33.3 |
| 7 | 42.5 | 37.2 | 37.6 |
| 8 | 46.4 | 40.4 | 40.8 |
| 9 | 49.6 | 42.6 | 43.7 |
| 10 | 52.0 | 44.5 | 46.3 |
| 11 | 54.3 | 45.7 | 48.4 |
| 12 | 57.8 | 46.5 | 51.1 |
| 13 | 62.8 | 47.1 | 56.1 |
| 14 | 68.2 | 51.8 | 61.5 |
| 15 | 72.3 | 57.4 | 66.4 |
| 16 | 77.3 | 62.4 | 70.8 |
| 17 | 82.5 | 67.1 | 75.1 |
| 18 | 87.0 | 71.0 | 78.4 |
| 19 | 91.2 | 74.1 | 81.9 |
| 20 | 94.8 | 76.0 | 84.6 |
| 21 | 97.9 | 78.5 | 86.4 |
| 22 | 99.2 | 79.9 | 87.8 |
| 23 | 100.0 | 81.1 | 88.7 |
| 24 | 100.0 | 81.8 | 89.5 |
| 25 | 100.0 | 83.4 | 89.5 |

As can be seen from Table 7, under the standard conditions of the experiments, a 100% conversion of glucose occurred only with Clintose and crystalline glucose. However, both Clearsweet and Royal glucose reached between 80 and 90% conversion.

EXAMPLE 8

Formation of Dry, Spray-Granulated Gluconic Acid/Gluconate and Comparison With Commercial Preparations The method of practicing the present invention is further illustrated by the following examples wherein the production of liquid or granular gluconic acid/gluconate of purity equivalent or better than commercial gluconic acid/gluconate is produced without any carbon treatment or crystallization.

Gluconic acid/gluconate obtained from the reactor as described in Experiment 3 of Example 2. The gluconic acid so obtained (in the form of liquid sodium gluconate) was then concentrated and crystals were separated by filtration (micro/ultra/polish) and dried at 37° C. These crystals were then used as a feed to produce a spray granulated gluconic acid/gluconate.

The spray-dryer used was a Uni-Glatt with Wurster Laboratory Model fluid bed dryer with a variable air temperature and flow through the bed. Approximately ¾ of the air holes outside the column were blocked off. The spraying nozzle was a twin fluid nozzle (Schlick).

The atomization air cap opening was 0.5 mm around the liquid nozzle and 1 mm below the opening of the liquid nozzle. The liquid nozzle opening was 1.2 mm. The air flow was sufficient to fluidize the bed and maintain flow through the Wurster column (110 CFM maximum).

Five hundred grams of sodium gluconate crystals (dried) were taken in the Uni-Glatt Dryer and 8480 grams of clear filtrate of gluconic acid/sodium gluconate (41.2° Brix) was then spray-coated onto the crystals with low inlet air flow due to low bulk density (0.5 grams/cc) of crystals (inlet air temperature of 100–105° C., air outlet temperature of 60–65° C.).

Initially, the air flow was 50 cfm (cubic feet per minute) being increased to 110 cfm as the particle density increased. Total drying time was 316 minutes.

The final particles were irregular spheres with smooth surfaces. Mass recovery in the process was 97.5%.

The above procedure was then repeated using each of the commercially-available gluconic acid preparations from the following sources: (1) Sigma Chemicals (USA); (2) ADM-Decatur (USA); (3) AKZO (USA); (4) Penta Mfg. (USA); and (5) PMP (USA). Sample (6) was the gluconic acid prepration prepared according to this Example.

The gluconic acid content of the different preparations was determined by HPLC using the protocol and under the same conditions as those described above in Example 1.

The color impurities were determined by measuring the absorbance (optical density) of 37.5% (w/w) solution gluconic acid in 5% (w/w) NaOH solution at 470 nm.

The results are summarized below in Table 8:

TABLE 8

| Sample | Optical Density | Purity %[1] |
|---|---|---|
| (1) | 0.003 | 100.0 |
| (2) | 0.029 | 95.7 |
| (3) | 0.029 | 99.5 |
| (4) | 0.014 | 98.9 |
| (5) | 0.051 | 100.0 |
| (6) | 0.001 | 100.0 |

[1]Purity % was 1 ml/min, 80° C., 0.01M Ca Acetate pH 5.5, HPX-87C

The results of Table 8 show that the quality of the spray-granulated gluconic acid preparations of the present invention without any further purifications, such as carbon treatment and crystallization was superior to the commercially available dry gluconic acid preparations.

What is claimed:

1. A process for the production of a low-dust spray-granulated gluconic acid, comprising the steps of:
   (a) obtaining a gluconic acid-containing solution wherein said solution is produced by the enzymatic conversion of glucose to gluconic acid, said conversion comprising providing a solution of glucose and adding to the solution from about 25 to about 30 glucose oxidase units (GOU) of soluble glucose oxidase/gram dissolved solids (ds.) of glucose in the solution and at least 1200 catalase units (CU) of soluble catalase/gram dissolved solids of glucose in the solution;

(b) obtaining gluconic acid crystals from the solution; and (c) spray-coating the gluconic acid crystals with liquid sodium gluconate in a spray-dryer, whereby a spray-granulated gluconic acid is obtained.

2. The process of claim 1, wherein the gluconic acid crystals are obtained from the gluconic acid-containing solution broth by concentrating and filtering the gluconic acid-containing solution.

3. The process of claim 1, wherein the catalase is naturally produced by a strain of *Micrococcus lysodeikticus*.

4. The process of claim 1, wherein the solution of glucose has from about 25% weight/weight (w/w/) ds. of glucose to about 60% (w/w) ds. of glucose.

5. The process of claim 1, wherein the solution of glucose has from about 30% (w/w/) ds. of glucose to about 50% (w/w) ds. of glucose.

6. The process of claim 1, wherein about 27 GOU of glucose oxidase/gram ds. of glucose is added to the solution.

7. The process of claim 1, wherein at least about 1279 CU of catalase/gram ds. of glucose is added to the solution.

8. The process of claim 1, wherein at least about 1559 CU of catalase/gram ds. of glucose is added to the solution.

9. The process of claim 1, wherein at least about 1999 CU of catalase/gram ds. of glucose is added to the solution.

10. The process of claim 1, wherein the glucose oxidase and the catalase are added to the solution of glucose in two equal doses, the first dose being added at the start of the reaction and the second dose being added halfway through the total intended time of the reaction.

11. The process of claim 1, wherein the solution of glucose is maintained at a pH of from about 5 to about 7.

12. The process of claim 11, wherein the solution of glucose is maintained at a pH of about 6.

13. The process of claim 1, wherein the temperature of the solution of glucose is maintained at from about 25° C. to about 40° C.

14. The process of claim 13, wherein the temperature of the solution of glucose is maintained at from about 30° C. to about 35° C.

15. The process of claim 1, wherein the pressure of the solution of glucose is maintained at about 1 bar.

16. The process of claim 1, further comprising maintaining an air flow through the solution during the reaction of about 1 volume gas per volume of reaction medium per minute (vvm).

17. The process of claim 1, wherein the catalase is naturally produced by a microbial or mammalian source.

18. The process of claim 1, wherein the catalase is naturally produced by a microbial source.

19. The process of claim 1, wherein the catalase is naturally produced by a strain of the species *Aspergillus niger*.

* * * * *